United States Patent
Bensaid et al.

(10) Patent No.: US 7,622,488 B2
(45) Date of Patent: Nov. 24, 2009

(54) USE OF A PYRAZOLE DERIVATIVE FOR PREPARING MEDICINES USEFUL FOR TREATING RENAL DISEASES

(75) Inventors: Mohammed Bensaid, Juvignac (FR); Jean-Marc Herbert, Tournefeuille (FR); Philip Janiak, Gif sur Yvette (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 11/832,861

(22) Filed: Aug. 2, 2007

(65) Prior Publication Data

US 2008/0015228 A1 Jan. 17, 2008

Related U.S. Application Data

(63) Continuation of application No. PCT/FR2006/000369, filed on Feb. 17, 2006.

(30) Foreign Application Priority Data

Feb. 23, 2005 (FR) .................................. 05 01919
May 12, 2005 (FR) .................................. 05 04798

(51) Int. Cl.
*A61K 31/445* (2006.01)
(52) U.S. Cl. .................................................... 514/326
(58) Field of Classification Search ................... 514/326
See application file for complete search history.

(56) References Cited

U.S. PATENT DOCUMENTS

| | | | | |
|---|---|---|---|---|
| 5,624,941 | A * | 4/1997 | Barth et al. | 514/326 |
| 6,432,984 | B1 * | 8/2002 | Barth et al. | 514/326 |
| 2004/0122033 | A1 | 6/2004 | Nargund et al. | |

FOREIGN PATENT DOCUMENTS

| | | |
|---|---|---|
| EP | 0656354 | 6/1995 |
| WO | WO 00/46209 | 8/2000 |
| WO | WO 2004/096132 | 11/2004 |
| WO | WO 2006/034489 | 3/2006 |

OTHER PUBLICATIONS

Bronander, K. A., et. al., Potential Role of the Endocannabinoid Receptor Antagonist Rimonabant in the Management of Cardiometabolic Risk: A Narrative Review of Available Data, Vascular Health and Risk Management (2007) vol. 3, No. 2, pp. 181-190.
Hollander, P., et. al., Endocannabinoid Blockade for Improving Glycemic Control and Lipids in Patient with Type 2 Diabetes Mellitus, The American Journal of Medicine (2007), vol. 120, No. 2A, pp. S18-S28.

* cited by examiner

*Primary Examiner*—Kevin Weddington
(74) *Attorney, Agent, or Firm*—Balaram Gupta

(57) ABSTRACT

This invention relates to use of a pyrazole-derived compound that is an antagonist of cannabinoid $CB_1$ receptors, alone or in combination with another active ingredient, for preparing medicinal products that are of use in the prevention and treatment of kidney diseases.

24 Claims, No Drawings

USE OF A PYRAZOLE DERIVATIVE FOR PREPARING MEDICINES USEFUL FOR TREATING RENAL DISEASES

This application is a continuation of International application No. PCT/FR2006/000,369, filed Feb. 17, 2006, which is incorporated herein by reference in its entirety; which claims the benefit of priority of French Patent Application No. 05/01, 919, filed Feb. 23, 2005 and French Patent Application No. 05/04,798, filed May 12, 2005.

The present invention relates to the use of a pyrazole-derived compound that is an antagonist for cannabinoid $CB_1$ receptors, for preparing medicinal products that are of use in the prevention and treatment of kidney diseases.

The term "kidney diseases" is intended to mean diabetic nephropathies, chronic renal failure, terminal kidney diseases, renal hypertrophy, renal hyperplasia, glomerulose sclerosis, glomerulose nephritis.

According to the present invention, the expression "pyrazole-derived cannabinoid receptor antagonist" is intended to mean a compound chosen from N-piperidino-5-(4-chlorophenyl)-1-(2,4-dichlorophenyl)-4-methylpyrazole-3-carboxamide, the international nonproprietary name of which is rimonabant, described in European Patent 656354, and N-piperidino-5-(4-bromophenyl)-1-(2,4-dichlorophenyl)-4-ethylpyrazole-3-carboxamide, the international nonproprietary name of which is surinabant, described in European Patent 1 150 961.

Clinical studies carried out with rimonabant have shown that it acts on food intake in quantitative and qualitative terms and reduces the body weight of obese patients (G. Le Fur, 2003, 35, First European Workshop on Cannabinoid Research, Madrid, Spain, 4-5 Apr. 2003 and Heshmati H. M. et al., Obesity Research, 2001, 9 (suppl. 3), 70.

It has now been found that a pyrazole-derived cannabinoid $CB_1$ receptor antagonist, chosen from rimonabant and N-piperidino-5-(4-bromophenyl)-1-(2,4-dichlorophenyl)-4-ethylpyrazole-3-carboxamide, protects kidney function.

Thus, according to the present invention, a pyrazole-derived compound that is an antagonist for cannabinoid $CB_1$ receptors, chosen from rimonabant and N-piperidino-5-(4-bromophenyl)-1-(2,4-dichlorophenyl)-4-ethylpyrazole-3-carboxamide, can be used for preparing medicinal products that are of use for preventing and treating kidney diseases.

The pharmaceutical compositions according to the present invention contain an effective dose of a pyrazole-derived compound that is an antagonist for cannabinoid $CB_1$ receptors, chosen from rimonabant and N-piperidino-5-(4-bromophenyl)-1-(2,4-dichlorophenyl)-4-ethylpyrazole-3-carboxamide, and also at least one pharmaceutically acceptable excipient.

Said excipients are chosen, according to the pharmaceutical form and the method of administration desired, from the usual excipients that are known to those skilled in the art.

In the pharmaceutical compositions of the present invention for oral, sublingual, subcutaneous, intramuscular, intravenous, topical, local, intratracheal, intranasal, transdermal or rectal administration, the active ingredient can be administered in unit administration form, as a mixture with conventional pharmaceutical excipients, to animals and to human beings, for the prevention or treatment of the disorders or of the diseases above.

Suitable unit administration forms include the forms for oral administration, such as tablets, soft or hard gelatin capsules, powders, granules and oral solutions or suspensions, the forms for sublingual, buccal, intratracheal, intraocular or intranasal administration and for administration by inhalation, the forms for topical, transdermal, subcutaneous., intramuscular or intravenous administration, the forms for rectal administration, and implants. For topical application, the compounds according to the invention can be used in creams, gels, ointments or lotions.

The forms for oral administration, such as gelatin capsules or tablets, are preferred.

More particularly, gelatin capsules or tablets containing rimonabant at a dose of between 5 and 50 mg, more particularly doses of 5 and 20 mg, are preferred.

Furthermore, for the use according to the present invention, a pyrazole-derived cannabinoid receptor antagonist, chosen from rimonabant and N-piperidino-5-(4-bromophenyl)-1-(2, 4-dichlorophenyl)-4-ethylpyrazole-3-carboxamide, can be combined with another active ingredient chosen from one of the following therapeutic classes:

a renin inhibitor;
an angiotensin II $AT_1$ receptor antagonist, alone or combined with a diuretic;
a converting enzyme inhibitor, alone or combined with a diuretic or with a calcium antagonist;
a calcium antagonist;
a beta-blocker, alone or combined with a diuretic or with a calcium antagonist;
another antihypertensive agent, such as an alpha-adrenergic agonist;
a blood lipid-lowering agent or a blood cholesterol-lowering agent;
an anti-diabetic agent;
a diuretic;
another anti-obesity agent.

Thus, a subject of the present invention is also the use of the pharmaceutical compositions containing, in combination, a pyrazole-derived cannabinoid $CB_1$ receptor antagonist, chosen from rimonabant and N-piperidino-5-(4-bromophenyl)-1-(2,4-dichlorophenyl)-4-ethylpyrazole-3-carboxamide, and another active ingredient chosen from the active ingredients of one of the following therapeutic classes:

an angiotensin II $AT_1$ receptor antagonist, alone or combined with a diuretic or with a calcium antagonist;
a converting enzyme inhibitor, alone or combined with a diuretic;
a calcium antagonist;
another antihypertensive agent, such as an alpha-adrenergic agonist;
a beta-blocker, alone or combined with a diuretic or with a calcium antagonist;
a blood lipid-lowering agent or a blood cholesterol-lowering agent;
an anti-diabetic agent;
a diuretic;
another anti-obesity agent;
for preparing medicinal products that are of use in the treatment and prevention of kidney diseases.

The expression "angiotensin II $AT_1$ receptor antagonist" is intended to mean a compound such as candesartan cilexitil, eprosartan, irbesartan, losartan potassium, olmesartan medoxomil, telmisartan or valsartan, it being possible for each of these compounds to itself be combined with a diuretic such as hydrochlorothiazide.

The expression "converting enzyme inhibitor" is intended to mean a compound such as alacepril, benazepril, captopril, cilazapril, enalapril, enalaprilat, fosinopril, imidapril, lisinopril, moexipril, perindopril, quinapril, ramipril, spirapril, temocapril, trandolapril or zofenopril, it being possible for each of these compounds to itself be combined with a diuretic such as hydrochlorothiazide or indapamide or with a calcium antagonist such as amlodipine, diltiazem, felodipine or verapamil.

The term "calcium antagonist" is intended to mean a compound such as amlodipine, aranidipine, benidipine, bepridil, cilnidipine, diltiazem, efonidipine hydrochloride ethanol, fasudil, felodipine, isradipine, lacidipine, lercanidipine hydrochloride, manidipine, mibefradil hydrochloride, nicardipine, nifedipine, nilvadipine, nimodipine, nisoldipine, nitrendipine, terodiline or verapamil.

The term "beta-blocker" is intended to mean a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propanolol, salmeterol, sotalol, talinolol, tertatolol, tilisolol, timolol, xamoterol or xibenolol.

The expression "other antihypertensive agent such as an alpha-adrenergic agonist" is intended to mean a compound such as clonidine, rilmenidine, maxonidine, methyldopa or guanfacine.

The term "diuretic" is intended to mean a compound such as hydrochlorothiazide, bendroflumethiazide, chlortalidone, cicletanine, indapamide or xipamide.

The expression "blood lipid-lowering agent" or "blood cholesterol-lowering agent" is intended to mean a compound chosen from fibrates such as alufibrate, beclobrate, bezafibrate, ciprofibrate, clinofibrate, clofibrate, etofibrate or fenofibrate; statins (HMG-CoA reductase inhibitors), such as atorvastatin, fluvastatin sodium, lovastatin, pravastatin, rosuvastatin or simvastatin, or a compound such as acipimox, aluminum nicotinate, azacosterol, cholestyramine, dextrothyroxine, meglutol, niceritrol, nicoclonate, nicotinic acid, beta-sitosterin or tiadenol. More particularly, a subject of the present invention is a pharmaceutical composition containing, in combination, rimonabant, atorvastatin or pravastatin, or preferably rimonabant and simvastatin. The term "antidiabetic agent" is intended to mean a compound belonging to one of the following classes: sulfonylureas, biguanidines, alpha-glucosidase inhibitors, thiazolidinediones or metiglinides, such as acarbose, acetohexamide, carbutamide, chlorpropamide, glibenclamide, glibornuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone or voglibose.

The term "other anti-obesity agent" is intended to mean a compound such as amfepramone, benfluorex, benzphetamine, indanorex, mazindole, mefenorex, methamphetamine, D-norpseudoephedrine, orlistat, sibutramine or another cannabinoid $CB_1$ receptor antagonist.

Most particularly, a subject of the present invention is the use of a pharmaceutical composition containing, in combination, rimonabant and an angiotensin II $AT_1$ receptor antagonist, in particular irbesartan, losartan or valsartan. More particularly, a subject of the present invention is the use of a pharmaceutical composition containing, in combination, rimonabant and irbesartan or N-piperidino-5-(4-bromophenyl)-1-(2,4-dichlorophenyl)-4-ethylpyrazole-3-carboxamide and irbesartan, and also the use of a pharmaceutical composition containing, in combination, rimonabant, irbesartan and hydrochlorothiazide, or N-piperidino-5-(4-bromophenyl)-1-(2,4-dichlorophenyl)-4-ethylpyrazole-3-carboxamide, irbesartan and hydrochlorothiazide.

According to another specific embodiment, a subject of the present invention is the use of a pharmaceutical composition containing, in combination, rimonabant and simvastatin, for preparing medicinal products that are of use for preventing and treating kidney diseases. According to another aspect of the invention, the pyrazole-derived cannabinoid receptor antagonist, chosen from rimonabant and N-piperidino-5-(4-bromophenyl)-1-(2,4-dichlorophenyl)-4-ethylpyrazole-3-carboxamide, and the other active ingredient combined can be administered simultaneously, separately or in a manner spread out over time.

The term "separate use" is intended to mean the administration of the two compounds of the composition according to the invention at the same time, each one included in a distinct pharmaceutical form.

The expression "use spread out over time" is intended to mean the successive administration of the first compound of the composition according to the invention, included in one pharmaceutical form, and then of the second compound of the composition according to the invention, included in a distinct pharmaceutical form.

In the case of this "use spread out over time", the period of time that elapses between the administration of the first compound of the composition according to the invention and the administration of the second compound of the same composition according to the invention does not generally exceed 24 hours; it may be longer if one or other of the compounds is provided in a pharmaceutical formulation that allows, for example, weekly administration.

The pharmaceutical forms, comprising either just one of the compounds constituting the composition according to the invention or the combination of the two compounds, or where appropriate, of three compounds, which can be used in the various types of uses described above, may, for example, be suitable for oral, nasal, parenteral or transdermal administration.

Thus, in the case of a "separate use" and of a "use spread out over time", two distinct pharmaceutical forms may be intended for the same route of administration or for a different route of administration (oral and transdermal or oral and nasal or parenteral and transdermal, etc.).

The invention therefore also relates to the use, for the treatment and prevention of kidney diseases, of a kit containing a pyrazole-derived cannabinoid $CB_1$ receptor antagonist, chosen from rimonabant and N-piperidino-5-(4-bromophenyl)-1-(2,4-dichlorophenyl)-4-ethylpyrazole-3-carboxamide, and another active ingredient or, where appropriate, two combined active ingredients, in which kit said pyrazole-derived cannabinoid $CB_1$ receptor antagonist and said active ingredient or, where appropriate, two combined active ingredients, are in distinct compartments and in similar or different packagings, and are intended to be administered simultaneously, separately or in a manner spread out over time.

EXAMPLE 1

Action of Rimonabant On the Protection of Renal Function In Obese Rats

The effect of a long-term treatment (12 months) with rimonabant was studied on Zucker rats having an established obesity.

The Zucker obese rat strain fa/fa is characterized by hyperphagia, obesity, dyslipidemia aid type 2 diabetes resulting in the gradual development of a nephropathy.

After 12 months, the Zucker fa/fa obese rats treated with the vehicle show marked hypertrophy of the kidneys and also severe renal failure. The deterioration of renal function is reflected by a marked increase in plasma urea and creatinine levels and by a marked reduction in creatinine clearance. In the Zucker fa/fa obese rats treated with rimonabant at 3 and 10 mg/kg/day per os for 12 months, it is observed that the increase in plasma urea and creatinine levels is decreased in a dose-dependent manner and that the creatinine clearance is partially restored. In parallel, the renal hypertrophy is significantly reduced in the group of rats treated with rimonabant.

Thus, it is observed that chronic treatment with rimonabant at 3 and 10 mg/kg/day per os significantly delays the protienuria.

The beneficial effects of rimonabant on renal function occur without any haemodynamic change. Thus, after 12 months of treatment at doses of 3 and 10 mg/kg/day, mean arterial pressure, left ventricular pressure, heart rate and contractility remain unchanged.

In parallel to the beneficial effects on the preservation of renal function and the correction of lipid metabolic disorders, rimonabant at 3 and 10 mg/kg/day per os very significantly prolongs the survival of the Zucker fa/fa obese rats. After 12 months of treatment, mortality reaches 64% in the group of untreated Zucker fa/fa obese rats, whereas it is limited to 20% ($p<0.01$) and 28% ($p<0.05$) in the obese Zucker rats treated with rimonabant at 10 and 3 mg/kg/day per os, respectively.

A group of Zucker fa/fa obese rats that were not treated, but received the same amount of food as the group treated with 10 mg/kg/day per os, was also formed (pair-fed group). This Zucker fa/fa obese/pair-fed group exhibits a mortality of 32% (not statistically significant compared with the nontreated Zucker fa/fa obese rats), that is earlier than that observed for the Zucker group treated with rimonabant at 10 mg/kg/day for 12 months.

By way of comparison, after 12 months of treatment with the vehicle, in animals showing no metabolic disorders (non-obese Zucker fa/fa rats), the mortality reaches 4%.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

The invention claimed is:

1. A method for the treatment of a kidney disease selected from the group consisting of chronic renal failure, terminal kidney disease, renal hypertrophy, renal hyperplasia, and glomerulose nephritis, comprising administering to a patient in need of said treatment a therapeutically effective amount of a compound that is an antagonist for cannabinoid $CB_1$ receptor, which is chosen from rimonabant and N-piperidino-5-(4-bromophenyl)-1-(2,4-dichlorophenyl)-4-ethylpyrazole-3-carboxamide.

2. The method according to claim 1, wherein the kidney disease is chronic renal failure.

3. The method according to claim 1, wherein the kidney disease is terminal kidney disease.

4. The method according to claim 1, wherein the kidney disease is renal hypertrophy.

5. The method according to claim 1, wherein the kidney disease is renal hyperplasia.

6. The method according to claim 1, wherein the kidney disease is glomerulose nephritis.

7. The method according to claim 1, wherein the compound that is an antagonist for cannabinoid $CB_1$ receptor is rimonabant.

8. The method according to claim 2, wherein the compound that is an antagonist for cannabinoid $CB_1$ receptor is rimonabant.

9. The method according to claim 3, wherein the compound that is an antagonist for cannabinoid $CB_1$ receptor is rimonabant.

10. The method according to claim 4, wherein the compound that is an antagonist for cannabinoid $CB_1$ receptor is rimonabant.

11. The method according to claim 5, wherein the compound that is an antagonist for cannabinoid $CB_1$ receptor is rimonabant.

12. The method according to claim 6, wherein the compound that is an antagonist for cannabinoid $CB_1$ receptor is rimonabant.

13. The method according to claim 7, wherein rimonabant is administered at a dose of about 5 mg to about 50 mg.

14. The method according to claim 7, wherein rimonabant is administered at a dose of about 5 mg to about 20 mg.

15. The method according to claim 8, wherein rimonabant is administered at a dose of about 5 mg to about 50 mg.

16. The method according to claim 8, wherein rimonabant is administered at a dose of about 5 mg to about 20 mg.

17. The method according to claim 9, wherein rimonabant is administered at a dose of about 5 mg to about 50 mg.

18. The method according to claim 9, wherein rimonabant is administered at a dose of about 5 mg to about 20 mg.

19. The method according to claim 10, wherein rimonabant is administered at a dose of about 5 mg to about 50 mg.

20. The method according to claim 10, wherein rimonabant is administered at a dose of about 5 mg to about 20 mg.

21. The method according to claim 11, wherein rimonabant is administered at a dose of about 5 mg to about 50 mg.

22. The method according to claim 11, wherein rimonabant is administered at a dose of about 5 mg to about 20 mg.

23. The method according to claim 12, wherein rimonabant is administered at a dose of about 5 mg to about 50 mg.

24. The method according to claim 12, wherein rimonabant is administered at a dose of about 5 mg to about 20 mg.

* * * * *